US008222233B2

(12) United States Patent
Yesair et al.

(10) Patent No.: US 8,222,233 B2
(45) Date of Patent: Jul. 17, 2012

(54) MODIFICATIONS OF SOLID 3-SN-PHOSPHOGLYCERIDES

(75) Inventors: David W. Yesair, Byfield, MA (US);
Walter A. Shaw, Birmingham, AL (US);
Stephen W. Burgess, Columbiana, AL (US); Robert Travis Mckee, Jacksonville, FL (US)

(73) Assignee: BioMolecular Products, Inc., Newburyport, MA (US)

( * ) Notice: Subject to any disclaimer, the term of this patent is extended or adjusted under 35 U.S.C. 154(b) by 0 days.

(21) Appl. No.: 13/087,738

(22) Filed: Apr. 15, 2011

(65) Prior Publication Data

US 2011/0190238 A1 Aug. 4, 2011

Related U.S. Application Data

(62) Division of application No. 12/142,370, filed on Jun. 19, 2008, now Pat. No. 7,947,306, which is a division of application No. 10/492,252, filed as application No. PCT/US02/32647 on Oct. 11, 2002, now Pat. No. 7,407,779.

(60) Provisional application No. 60/328,660, filed on Oct. 11, 2001.

(51) Int. Cl.
*A61K 31/662* (2006.01)
*A61K 47/12* (2006.01)
*A61K 9/00* (2006.01)
*A61P 11/00* (2006.01)

(52) U.S. Cl. ........ 514/114; 424/94.6; 424/484; 514/784

(58) Field of Classification Search .......... 424/94.6, 424/484; 514/784, 54, 114
See application file for complete search history.

(56) References Cited

U.S. PATENT DOCUMENTS

| 4,849,132 A | 7/1989 | Fujita et al. |
| 4,874,795 A | 10/1989 | Yesair |
| 5,314,921 A | 5/1994 | Yesair |
| 5,571,517 A | 11/1996 | Yesair |
| 5,612,190 A | 3/1997 | Arita et al. |
| 5,707,873 A | 1/1998 | Yesair |
| 5,716,814 A | 2/1998 | Yesair |
| 5,741,822 A | 4/1998 | Yesair |
| 5,891,466 A | 4/1999 | Yesair |
| 5,972,911 A | 10/1999 | Yesair |
| 6,426,069 B1 | 7/2002 | Yesair |
| 7,407,779 B2 | 8/2008 | Yesair et al. |
| 2009/0017119 A1 | 1/2009 | Yesair et al. |

OTHER PUBLICATIONS

Bent, Elyssa D. et al., "Quantification of the interactions among fatty acid, lysophosphatidylcholine, calcium, dimyristoyl-phosphatidylcholine vesicles, and phospholipase $A_2$," *Biochemica et Biophysica Acta* 1995; 1254:349-360.
Gregory, J.K. et al., "The Water Dipole Moment in Water Clusters," *Science* Feb. 7, 1997; 275:814-817.
Hauser, H., "The Conformation of the Polar Group of Lecithin and Lysolecithin," *Journal of Colloid and Interface Science* Apr. 1976; 55(1):85-93.
Holt, Peter R. et al., "A Liquid Crystalline Phase in Human Intestinal Contents During Fat Digestion," *Lipids* 1986; 21(7):444-446.
Hui, S.W., "X-ray Diffraction Evidence for Fully Interdigitated Bilayers of 1-Stearoyllysophosphatidylcholine," *Biochemistry* 1986; 25:1330-1335.
Koo, Sung I. et al., "Effect of Zinc Deficiency on Intestinal Transport of Triglyceride in the Rat," *The Journal of Nutrition* May 1977; 107(5):909-919.
Koo, Sung I. et al., "Effect of marginal zinc deficiency on the morphological characteristics of intestinal nascent chylomicrons and distribution of soluble apoproteins of lymph chylomicrons," *The American Journal of Clinical Nutrition* Oct. 1985; 42:671-680.
Lepage, Guy et al., "Effect of an organized lipid matrix on lipid absorption and clinical outcomes in patients with cystic fibrosis," *The Journal of Pediatrics* Aug. 2002; 141(2):178-185.
Rand, R.P. et al., "Structural Dimensions and Their Changes in a Reentrant Hexagonal-Lamellar Transition of Phospholipids," *Biophysical Journal* Jun. 1994; 66:2127-2138.
Rosevear, F.B. et al., "The Microscopy of the Liquid Crystalline Neat and Middle Phases of Soaps and Synthetic Detergents," *The Journal of the American Oil Chemists' Society* Dec. 1954; 31(12):628-639.
Robinson, N. et al., "The Physical Properties of Lysolecithin and its Sols," *Journal of Pharmacy and Pharmacology* 1959; 11:304-313.
Saunders, L., "Molecular Aggregation in Aqueous Dispersions of Phosphatidyl and Lysophosphatidyl Cholines," *Biochem. Biophys. Acta.* 1996; 125:70-74.
Small, D.M., "The Physical Chemistry of Lipids from Alkanes to Phospholipids," Handbook of Lipid Research 4, Plenum Press, New York, NY 1986, pp. 386-392, 475-517.
Wells, M.A. et al., "Studies on Phospholipase A.I. Isolation and Characterization of Two Enzymes from *Crotalus adamanteus* Venom," *Biochemistry* 1696; 8(1):414-424, Pub Jan. 1969.
[No Author Listed] Nutritional Reviews; Jun. 1984; 6(42):220-222.

*Primary Examiner* — Herbert J Lilling
(74) *Attorney, Agent, or Firm* — Wolf, Greenfield & Sacks, P.C.

(57) ABSTRACT

Methods for hydrolyzing solid ungranulated lysophosphatidylcholine with phospholipase $A_2$ are provided. Also disclosed are methods for making a lipid matrix of lysophosphatidylcholine, monoglyceride and fatty acid, and lipid matrices of particular structure.

8 Claims, 7 Drawing Sheets

PHOSPHATIDYLCHOLINE (LAMELLAR)  PHOSPHATIDYLETHANOLAMINE (HEXAGONAL)  LIPID MATRIX (UNKNOWN STRUCTURE)

LAMELLAR PHASE

HEXAGONAL PHASE

INVERSE HEXAGONAL PHASE

MODIFICATIONS OF SOLID 3-SN-PHOSPHOGLYCERIDES

RELATED APPLICATIONS

This application is a divisional of U.S. application Ser. No. 12/142,370, filed Jun. 19, 2008 and now issued as U.S. Pat. No. 7,947,306, which is a divisional of U.S. application Ser. No. 10/492,252, filed Aug. 5, 2004 and now issued as U.S. Pat. No. 7,407,779, which was a national stage filing under 35 U.S.C. §371 of PCT International application PCT/US02/32647, filed Oct. 11, 2002, which was published under PCT Article 21(2) in English, which claims the benefit under 35 USC §119 of U.S. provisional application Ser. No. 60/328,660, filed Oct. 11, 2001, all of which are incorporated herein by reference.

FIELD OF THE INVENTION

This invention relates generally to the field of phospholipid hydrolysis. In particular, this invention relates to an improved method of phospholipase $A_2$ hydrolysis of solid ungranulated phosphatidylcholine to produce lysophosphatidylcholine. This invention also relates to a method of making a lipid matrix comprising lysophosphatidylcholine, monoglyceride, and fatty acid, as well as lipid matrix compositions having a non-lamellar structure and high viscosity.

BACKGROUND OF THE INVENTION

Enzymatic conversion of phosphatidylcholine to lysophosphatidylcholine has been known since the early 1900's. Early investigations of the degradation of lecithin (phosphatidylcholine) by snake venom extracts demonstrated that the action of snake venom hemolysis is upon the lecithin portion of the cell membrane. In 1935, Hughes demonstrated that the hydrolysis of a unimolecular film of lecithin to lysolecithin (lysophosphatidylcholine) is dependent on factors such as pH, temperature and the surface concentration of the lecithin molecules. Packing of the lecithin molecules in the unimolecular layer greatly decreased the rate of hydrolysis. Hanahan demonstrated that an ether-soluble complex between egg phosphatidylcholine and phospholipase $A_2$ resulted in the release of unsaturated fatty acid and lysophosphatidylcholine. Hydrolysis of phosphatidylcholine by phospholipase $A_2$ could not be detected when 95% ethyl alcohol, chloroform or petroleum ether were used as solvents. Experiments performed by Dawson, reported in 1963, also found that phospholipase $A_2$ hydrolyzed phosphatidylcholine to lysophosphatidylcholine and a single fatty acid molecule. Dawson determined that the enzymatic activity was dependent on the presence of calcium ions, and that the addition of ether or butanol stimulated the phospholipase $A_2$ activity. British patent 1,215,868 to Unilever Ltd. described a further modification of the hydrolysis of phospholipid by phospholipase $A_2$, conducting the reaction in the presence of fat (oils).

The processes of phosphatidylcholine hydrolysis disclosed in the prior art suffer from several shortcomings, including incomplete hydrolysis and production of unwanted side products in the hydrolysis reaction. The deficiencies of the prior art methods are severe because the presence of unreacted starting materials or unwanted side products represent an unacceptable level of contaminants in the final reaction product. These unwanted constituents must be removed from the reaction product in order to obtain the desired product, lysophosphatidylcholine, thus necessitating additional purification steps.

The prior art methods described above produce a maximal yield of lysophosphatidylcholine of approximately 70% of the starting phosphatidylcholine. Dawson showed that the addition of ether was required to stimulate the phospholipase $A_2$ activity in the hydrolysis of phosphatidylcholine to the maximum yield of about 60-70%. The maximum yield of lysophosphatidylcholine was obtained when 8% diethyl ether (vol./vol.) in aqueous buffer was the reaction medium; using this reaction medium a two-phase system was observed. Dawson also found that 6% butanol (vol./vol.) could substitute for diethyl ether in the reaction medium to enhance yield of lysophosphatidylcholine, but ethanol and methylisobutylhexane were ineffective for increasing hydrolysis of phosphatidylcholine. Dawson concluded that the stimulatory effect of ether (or butanol) on hydrolysis of phosphatidylcholine was probably due to surface dilution of the closely packed phosphatidylcholine molecules oriented at the lipid interface and a removal of inhibitory fatty acid carbonyl groups from the interface. This conclusion was supported by evidence that addition of fatty acids inhibited the enzymatic hydrolysis of phosphatidylcholine (Dawson). Inhibition of the reaction by added fatty acid resulted either from inhibiting the removal of the fatty acid from the interface, or from formation of a calcium ion—fatty acid chelate, i.e., removal of $Ca^{2+}$ ions required for phospholipase $A_2$ activity. Dawson believed that the removal of calcium ions was the more likely explanation because the further addition of ether to form two phases and solubilize the additional fatty acid did not promote hydrolysis of phosphatidylcholine, whereas increasing the calcium concentration ten fold did partially relieve the inhibition. It was also shown that the phospholipase $A_2$ enzyme purified from cobra venom was dependent on the presence of calcium ions for hydrolysis activity. The requirement for calcium ions in the hydrolysis reaction by phospholipase $A_2$ and the association of calcium ions with fatty acids released by the hydrolysis of phosphatidylcholine is well known in the art (Novo Nordisk).

Yesair described methods for the preparation of mixed lipid particles useful in the delivery of drugs and for providing readily absorbable calories to an individual (U.S. Pat. Nos. 4,874,795 and 5,314,921). These methods involve the mixing of lysophosphatidylcholine, monoglyceride and fatty acid in specific molar ratios. Although easily performed, these previous methods use costly, isolated, highly purified lysophosphatidylcholine, thus adding to the expense of the final mixed lipid particle product.

Yesair subsequently described methods by which phosphatidylcholine is more efficiently converted to lysophosphatidylcholine (U.S. Pat. No. 5,716,814). The described methods result in more efficient use of phosphatidylcholine and yield fewer unwanted side products (such as glycerophosphatidylcholine) and contaminants (such as unhydrolyzed phosphatidylcholine) in the final reaction product. The use of the described methods in which the end products are in a more pure form results in substantial cost savings and time savings due to a reduced need for the purification of the end products. These methods require, however, the use of partially purified phosphatidylcholine in granulated form. While ability to use of this form of phosphatidylcholine represents an improvement over prior methods, there remains a need to reduce the cost of production of lysophosphatidylcholine. A method which utilizes less highly processed phosphatidylcholine as a starting material would reduce the need for the use of a relatively more expensive granulated preparation of phosphatidylcholine as a starting material, thus reducing the overall costs for the final lysophosphatidylcholine product and for mixed lipid particle products prepared using lysophosphatidylcholine.

SUMMARY OF THE INVENTION

The invention involves improvements in enzymatic modification of 3-sn-phosphoglyceride molecules, particularly hydrolysis of phosphatidylcholine. In a preferred embodiment, the present invention provides methods whereby solid ungranulated blocks of phosphatidylcholine can be converted to lysophosphatidylcholine with nearly 100% efficiency. Further, the hydrolysis of phosphatidylcholine according to the present invention results in production of small quantities, if any, of unwanted side products. The present invention provides a method which reduces the cost of making lysophosphatidylcholine by converting ungranulated phosphatidylcholine.

The present invention also provides lipid matrix compositions having particular structure and associated physical properties. These compositions are useful, inter alia, as drug delivery compositions.

According to one aspect of the invention, methods for modifying ungranulated/solid matrix 3-sn-phosphoglyceride molecules are provided. The methods include forming a reaction mixture by contacting ungranulated/solid matrix 3-sn-phosphoglyceride molecules with an amount of phospholipase $A_2$ sufficient to modify an ester bond of the 3-sn-phosphoglyceride molecules, and incubating the reaction mixture to modify the 2-acyl bond. In certain preferred embodiments, the ester bond modification is hydrolysis. In other preferred embodiments, the 3-sn-phosphoglyceride is phosphatidylcholine.

In some embodiments, the methods also include adding one or more fatty acids to the reaction mixture. Preferably the fatty acids include 8-24 carbon atoms and 0-6 cis or trans double bonds with or without methyl branches and/or hydroxyl groups at any carbon atom.

In other embodiments, the methods also include adding one or more agents selected from the group consisting of monoglyceride; diglyceride; polyglycerol fatty acid ester; sucrose fatty acid ester; sorbitan fatty acid ester; glycerol and other alcohol functional groups including serine and ethanolamine; and solvents. Preferably the one or more agents is monoglyceride. Preferred monoglycerides include monoglycerides having an acyl group; the acyl group preferably includes 8-24 carbon atoms and 0-6 cis or trans double bonds with or without methyl branches and/or hydroxyl groups at any carbon atom.

In still other embodiments, the methods include adding calcium ions or other multivalent ions.

According to another aspect of the invention, methods for making lysophosphoglyceride are provided. The methods include contacting ungranulated/solid matrix 3-sn-phosphoglyceride with phospholipase $A_2$ to form a reaction mixture, and recovering lysophosphoglyceride formed in the reaction mixture.

In preferred embodiments, the reaction mixture further contains one or more fatty acids. Preferably the fatty acids include 8-24 carbon atoms and 0-6 cis or trans double bonds with or without methyl branches and/or hydroxyl groups at any carbon atom.

In other preferred embodiments, the reaction mixture further contains an agent selected from the group consisting of monoglyceride; diglyceride; polyglycerol fatty acid ester; sucrose fatty acid ester; sorbitan fatty acid ester; glycerol and other alcohol functional groups including serine and ethanolamine; and solvents. Preferably the agent is monoglyceride. More preferably, the monoglyceride has an acyl group and the acyl group comprises 8-24 carbon atoms and 0-6 cis or trans double bonds with or without methyl branches and/or hydroxyl groups at any carbon atom.

In certain of the foregoing methods for making lysophosphatidylcholine, the step of recovering comprises separating lysophosphoglyceride from one or more reaction mixture constituents selected from the group consisting of 3-sn-phosphoglyceride, fatty acid, and the agent.

In some embodiments, the step of separation of lysophosphoglyceride from the one or more reaction mixture constituents comprises extraction with acetone.

In other embodiments, the 3-sn-phosphoglyceride in the reaction mixture is greater than about 40% by weight of the mixture, greater than about 50% by weight of the mixture, or greater than about 60% by weight of the mixture.

According to still another aspect of the invention, lysophosphoglyceride produced by the forgoing methods is provided.

In preferred embodiments of any of the foregoing claims, the lysophosphoglyceride is lysophosphatidylcholine, and/or the 3-sn-phosphoglyceride is phosphatidylcholine.

Methods for making a composition containing lysophosphoglyceride, monoglyceride and fatty acid are provided according to another aspect of the invention. The methods include contacting a reaction mixture of ungranulated/solid matrix 3-sn-phosphoglyceride and monoglyceride with phospholipase $A_2$, and recovering a lipid complex containing lysophosphoglyceride, monoglyceride and fatty acid. The molar ratio of lysophosphoglyceride to the sum of monoglyceride and fatty acid in the recovered lipid complex composition is between 1:3 and 1:12. Preferably the molar ratio of lysophosphoglyceride to the sum of monoglyceride and fatty acid in the recovered lipid complex composition is between 1:5 and 1:6.

In some embodiments the recovered lipid complex composition has a lysophosphoglyceride:monoglyceride:fatty acid molar ratio between 1:4:2 and 1:2:4. Preferably the recovered lipid complex composition has a lysophosphoglyceride:monoglyceride:fatty acid molar ratio selected from the group consisting of 1:4:2, 1:3:3 and 1:3:2.

In certain embodiments the monoglyceride is derived from natural triglyceride. In other embodiments, the step of recovering the lipid complex comprises removal of water.

In preferred embodiments of the foregoing methods, the lysophosphoglyceride is lysophosphatidylcholine.

According to yet another aspect of the invention, drug delivery compositions are provided. The drug delivery compositions include a lipid matrix, at least part of which is in a lamellar phase, and a pharmaceutically acceptable carrier.

According to a further aspect of the invention, other drug delivery compositions are provided. The drug delivery compositions include a lipid matrix, at least part of which is in a hexagonal phase or an inverse hexagonal phase, and a pharmaceutically acceptable carrier.

According to a still another aspect of the invention, additional drug delivery compositions are provided. The drug delivery compositions include a lipid matrix, at least part of which is in a phase other than a lamellar phase, hexagonal phase or inverse hexagonal phase, and a pharmaceutically acceptable carrier.

In certain embodiments of the foregoing drug delivery compositions, the lipid matrix includes from about 0 to about 8 moles of water per mole of lipid. In some preferred embodiments, the lipid matrix includes at least about 1 mole of water per mole of lipid. In other preferred embodiments, the lipid matrix includes at least about 3 moles of water per mole of lipid. In still other preferred embodiments, the lipid matrix includes at least about 8 moles of water per mole of lipid.

In other embodiments of the foregoing drug delivery compositions, the lipid matrix comprises lysophosphoglyceride, monoglyceride and fatty acid, and the molar ratio of lysophosphoglyceride to the sum of monoglyceride and fatty acid in the lipid matrix is between 1:3 and 1:12. Preferably the molar ratio of lysophosphoglyceride to the sum of monoglyceride and fatty acid in the lipid matrix is between 1:5 and 1:6. In certain preferred embodiments, the lipid matrix has a lysophosphoglyceride:monoglyceride:fatty acid molar ratio between 1:4:2 and 1:2:4. More preferably, the lipid matrix has a lysophosphoglyceride:monoglyceride:fatty acid molar ratio selected from the group consisting of 1:4:2, 1:3:3 and 1:3:2.

In some preferred embodiments of the foregoing drug delivery compositions, the lysophosphoglyceride is lysophosphatidylcholine. In other embodiments, the drug delivery compositions also include one or more water soluble or water insoluble pharmaceutical compounds.

According to still another aspect of the invention, a lipid matrix is provided. The lipid matrix includes lysophosphatidylcholine, monoglyceride and fatty acids, and has a viscosity indicative of a non-Newtonian fluid. In embodiments in which the lipid matrix includes water, the molar ratio of water:lipid matrix preferably is less than or equal to about 8:1.

In another aspect, the invention provides methods for making a comestible lipid matrix composition in a reactor vessel. The methods include preparing a lipid matrix containing lysophosphatidylcholine, monoglyceride and fatty acids, adding a dilute aqueous acid to the lipid matrix in the reactor vessel, mixing and heating the reactor vessel contents to prepare a protonated aqueous lipid matrix, combining the protonated aqueous lipid matrix with comestible components in a reactor vessel, and mixing the comestible components and the protonated aqueous lipid matrix in the reactor vessel to make a comestible lipid matrix composition. In some embodiments, about 8 moles of water are added per mole of lipid matrix. In other embodiments, the reactor vessel contents are heated to about 50-60° C. In yet other embodiments, the comestible components include compounds selected from the group consisting of protein, sugar and starch.

According to another aspect of the invention, methods for treating cystic fibrosis are provided. The methods include administering to a subject in need of such treatment an effective amount of any of the foregoing compositions. In preferred embodiments, a physiological parameter of the subject related to the cystic fibrosis is improved. Preferred physiological parameters include height-for-age Z score, weight-for-age Z score, forced expiratory volume, energy intake from diet, essential fatty acid status, fat soluble vitamin status and retinol binding protein status.

According to still another aspect of the invention, nutritional supplements are provided. The nutritional supplements include an effective amount of any of the foregoing compositions. In preferred embodiments, the nutritional supplement are used for the treatment of cystic fibrosis. Use of any of the foregoing compositions in the preparation of medicaments, particularly for treatment of cystic fibrosis, also is provided.

These and other aspects and objects of the invention will be described in further detail in connection with the Detailed Description of the Invention.

BRIEF DESCRIPTION OF THE FIGURES

FIG. 9 shows schematic representations of a lipid matrix.

DETAILED DESCRIPTION OF THE INVENTION

Figure 1:
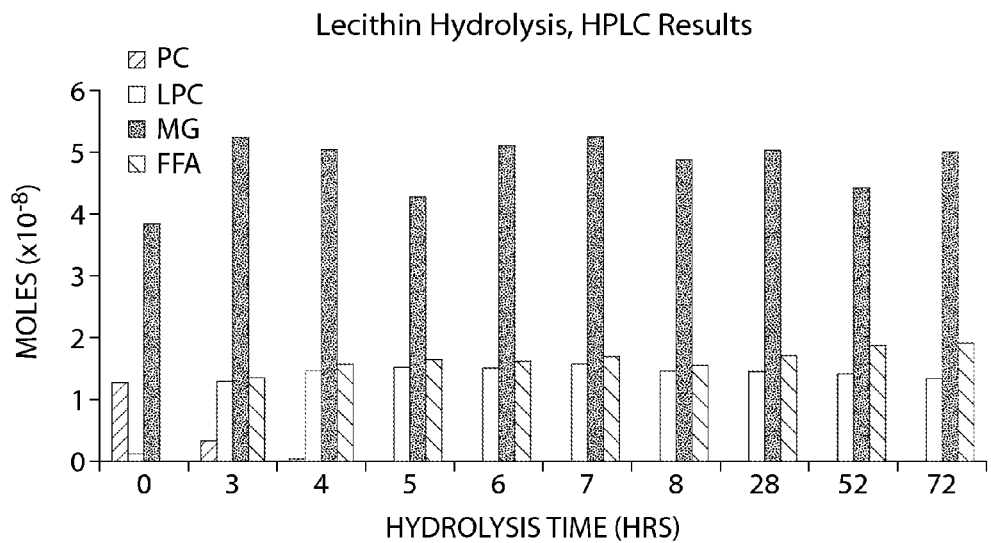
FIG. 1 depicts the composition over time of the phosphatidylcholine hydrolysis reaction mixture without added monoolein.

The invention includes improved methods for making lysophosphatidylcholine which involve hydrolyzing ungranulated/solid matrix phosphatidylcholine by contacting it with a phospholipase, preferably phospholipase $A_2$, in a reaction mixture. Phospholipase $A_2$ is preferred because the lysophosphatidylcholine produced by hydrolysis of phosphatidylcholine at the 2-position is the biologically preferred lysophosphatidylcholine (in contrast with lysophosphatidylcholine produced by hydrolysis of phosphatidylcholine at the 1-position). In broader aspects of the invention, methods of modifying 3-sn-phosphoglycerides are provided. In such methods, an amount of phospholipase that is sufficient to modify one or more ester bond linkages (designated A, B, C, and D) of the 3-sn-phosphoglyceride molecules is combined with ungranulated/solid matrix 3-sn-phosphoglyceride. The preferred embodiments described herein, pertaining to the hydrolysis of phosphatidylcholine by phospholipase A2, are exemplary of the more general methods provided by the invention.

In certain aspects of the methods, the reaction mixture can include fatty acids and/or an agent. The formed lysophosphatidylcholine optionally may be separated from the added agent and/or the fatty acids which are liberated by the action of phospholipase $A_2$ on phosphatidylcholine. The method enables substantially complete hydrolysis of inexpensive ungranulated/solid matrix phosphatidylcholine to lysophosphatidylcholine in a single step. If desired, the agent may be monoglyceride and the resulting lipid matrix of lysophosphatidylcholine, monoglyceride and fatty acids may be separated from the phospholipase $A_2$, trace unreacted phosphatidylcholine, water, organic solvents, and any impurities present in the reaction mixture. The resulting lipid matrix, in defined molar ratios, is useful as a caloric medical food to provide both polyunsaturated fatty acids and the absorbable form of choline (lysophosphatidylcholine), and is useful as a drug delivery system.

The following abbreviations are used herein for components of the described methods and lipid matrices: phosphatidylcholine (PC), lysophosphatidylcholine (LPC), monoglyceride (MG), fatty acids (FA) and phospholipase $A_2$ ($PLA_2$).

The starting material for the method is phosphatidylcholine, a phospholipid composed of a polar hydrophilic head group of choline, phosphate and glycerol linked to a nonpolar hydrophobic tail group consisting of two fatty acid molecules. Phosphatidylcholine may be obtained with specific fatty acid groups, or with a mixture of various fatty acid groups.

One of the advantages of the presently disclosed methods is the ability to use ungranulated/solid matrix phosphatidylcholine as a starting material. This kind of phosphatidylcholine, although significantly less expensive than purified, granulated phosphatidylcholine used in previous enzymatic methods of phosphatidylcholine hydrolysis, has not previously been used to make lysophosphatidylcholine because it was thought to be impossible to hydrolyze efficiently due to the small surface area of a solid matrix (e.g., block) of phosphatidylcholine as compared to the combined surface area of the individual granules of granulated phosphatidylcholine.

Previous methods of phosphatidylcholine hydrolysis (e.g., U.S. Pat. No. 5,716,814 to Yesair) hydrolyzed an aqueous dispersion of granulated phosphatidylcholine. In contrast, the present disclosure demonstrates, unexpectedly, that the hydrolysis of a solid block of phosphatidylcholine can be successfully accomplished. Even more surprisingly, it now has been determined that an economical ungranulated/solid matrix phosphatidylcholine can be hydrolyzed as efficiently as a more expensive granulated preparation using an efficient mixing apparatus (e.g., Littleford-Day reactor). Examples of ungranulated/solid matrix phosphatidylcholine is Nattermann 8729, Phospholipon® 80 and Phospholipon® 90, all of which are soy phosphatidylcholine preparations.

As disclosed herein, a reaction mixture of phosphatidylcholine and phospholipase $A_2$ is prepared by combining these reaction components. The term "mixture" merely indicates that the components are in contact with one another.

Other components can be added to the reaction mixture, including agent(s) (e.g., monoglyceride(s)), fatty acid(s), multivalent ions (e.g., calcium), buffer salts (e.g., sodium bicarbonate), acids or bases, and water.

The addition of an agent is believed to achieve several purposes. First, the molecules of the agent are believed to separate the phosphatidylcholine molecules to allow greater access to the phosphatidylcholine by phospholipase $A_2$, thus enabling complete hydrolysis to lysophosphatidylcholine. Second, addition of the agent is believed to maintain the proper structure during the hydrolysis reaction, i.e., polar head group associated with the bulk water phase containing enzyme. Third, addition of the agent is believed to maintain fluidity of the phosphatidylcholine bilayer to enhance hydrolysis by phospholipase $A_2$. Fourth, addition of the agent is believed to remove the hydrolytic products (LPC and FA) from the surface of the ungranulated/solid matrix. Thus, any agent which has one or more of the aforementioned characteristics is believed suitable for adding to phosphatidylcholine to facilitate hydrolysis by phospholipase $A_2$. It is preferable that the agent be selected from amongst the group consisting of monoglyceride, diglyceride, polyglycerol fatty acid ester, sucrose fatty acid ester, sorbitan fatty acid ester, glycerol and other alcohol functional groups. Most preferably, the agent is monoglyceride.

Monoglyceride is composed of a glycerol head group to which one fatty acid acyl group is attached. Preferred acyl groups of monoglyceride useful in the invention may include 8-24 carbon atoms and 0-6 cis or trans double bonds with or without methyl branches and/or hydroxyl groups at any carbon atom. Acyl groups of monoglyceride preferably include 1-4 double bonds in the carbon chain. The monoglyceride may be highly purified or may be added in a crude form, depending on the needs of the user and the tolerance for impurities in the reaction mixture. Monoglycerides useful in the invention may represent a mixture of monoglyceride molecules having different size and saturation-state acyl groups, or the monoglyceride may represent only a single type of acyl group, e.g., mono-olein, mono-palmitin. Examples of a mixture of monoglycerides useful in the invention include Dimodan™ LSK, Dimodan™ OK and flaxseed oil monoglycerides (Danisco Cultor, New Century, Kans.).

Diglyceride molecules are also useful in the method of the invention for enhancing the hydrolysis of phosphatidylcholine by phospholipase $A_2$. A diglyceride molecule consists of a glycerol head group to which two fatty acid acyl groups are attached. As with the acyl group of monoglyceride, the acyl groups of diglyceride can include 8-24 carbon atoms and 0-6 cis or trans double bonds with or without methyl branches and/or hydroxyl groups at any carbon atom. The acyl groups of diglyceride preferably have carbon chain links from 8 to 22 carbon atoms and 1 to 4 unsaturations. As with monoglyceride, the specific acyl groups, purity, and mixture of diglyceride molecules useful in the invention depend on the requirements of the individual user. Any combination or type of diglyceride molecules is contemplated by the invention, so long as the hydrolysis of phosphatidylcholine is enhanced.

Other agents such as polyglycerol fatty acid esters, sorbitan fatty acid esters, sucrose fatty acid esters and glycerol may also enhance the hydrolysis of phosphatidylcholine by removing the hydrolytic products from the solid PC surface and by modulating the surface structure and/or fluidity of the solid PC. Such compounds are described in U.S. Pat. No. 4,849,132. A polyglycerol fatty acid ester molecule consists of mono-, di- or polyesters of fatty acids with 4-12 polymerized glycerol molecules. A sorbitan fatty acid ester molecule consists on mono-, di- or polyesters of fatty acids with sorbitol, sorbitan and sorbide. A sucrose fatty acid ester molecule consists of mono-, di- or polyesters of fatty acids with sucrose. As with the acyl group of monoglyceride, the fatty acids/acyl groups of polyglycerol fatty acid ester, sorbitan fatty acid ester and sucrose fatty acid ester can include 8-24 carbon atoms and 0-6 cis or trans double bonds with or without methyl branches and/or hydroxyl groups at any carbon atom. Preferably these acyl groups have carbon chains of 8-22 carbon atoms and 1-4 unsaturations. As above, the specific acyl groups, purity, and mixture of agent molecules useful in the invention depend on the requirements of the individual user.

Any single agent or mixture of different agents which enhances hydrolysis of phosphatidylcholine is contemplated as useful for the invention. The aforementioned agents are available commercially from a variety of sources.

Phosphatidylcholine is hydrolyzed to lysophosphatidylcholine by the action of phospholipase $A_2$, which severs the ester bond linking a fatty acid group to the 2-position of the glycerol in the head group of phosphatidylcholine. Phospholipase $A_2$ may be purified from a variety of sources, or it may be obtained from commercial sources (e.g., Lecitase™ Novo Nordisk, Denmark). For full activity, phospholipase $A_2$ is believed to require the presence of $Ca^{2+}$ ions in the reaction mixture. While typically there is a low level of $Ca^{2+}$ ions in the commercial phospholipase $A_2$ preparations such that phospholipase $A_2$ is active, it is preferred that $Ca^{2+}$ ions be added to the reaction mixture for full activity. It should be noted that $Ca^{2+}$ ions are depleted from the reaction mixture by ionic bonding with the acid group of fatty acids liberated during hydrolysis of phosphatidylcholine. Therefore it is preferred that sufficient $Ca^{2+}$ ions are added to the reaction mixture to maintain full activity of phospholipase $A_2$. In this invention, it is most preferable that the user supplement the calcium ion concentration to achieve a molar ratio of calcium ion:phosphatidylcholine of at least 0.18:1.

Phospholipase $A_2$ catalyzes the hydrolysis of the 2-acyl bond of 3-sn-phosphoglycerides. Accordingly, the present methods that utilize phospholipase $A_2$ in the hydrolysis of phosphatidylcholine can be used for hydrolysis of other 3-sn-phosphoglycerides. Adjustments in reaction conditions for specific 3-sn-phosphoglyceride molecules other than phosphatidylcholine can be made in accordance with the known properties of phospholipases and/or with routine experimentation.

It will be recognized by persons of skill in the art that other ions may be substituted for the $Ca^{2+}$ ions in order to maintain full activity of the phospholipase $A_2$ enzyme. While not all ions may substitute for $Ca^{2+}$ ions in this reaction, the specific type and concentration of ions adequate for maintenance of phospholipase $A_2$ activity may be tested using routine methods by one of ordinary skill in the art.

As disclosed above, the method of making lysophosphatidylcholine includes forming a reaction mixture of phosphatidylcholine and phospholipase $A_2$. In contrast to previous methods of making LPC, which required granulation of PC and formation of an aqueous dispersion of the PC in water, the present methods do not require PC granulation.

Other reaction conditions, such as pH, time and temperature, may be varied to achieve optimal hydrolysis of phosphatidylcholine. For example, phospholipase $A_2$ has a pH optimum of pH 8-9 which should be maintained to retain maximal enzyme activity. During the progress of the reaction, as fatty acids are released by hydrolysis of phosphatidylcholine, the pH of the reaction mixture may change. Such a change of pH may require the addition of base to maintain the optimal range of pH 8-9. Any base which effectively raises the pH to the optimal range without interfering with the hydrolysis of phosphatidylcholine may be used. Aqueous sodium hydroxide or sodium bicarbonate may be used for this purpose. Other formulations of sodium hydroxide or other bases may be employed for the same purpose. If the particular reaction conditions employed result in an increase in pH, then it is contemplated that acid may be added to maintain optimal pH.

Hydrolysis of 3-sn-phosphoglycerides (e.g., phosphatidylcholine) by phospholipase $A_2$ will proceed at many temperatures less than or equal to about 80° C., such as at the optimal temperature for phospholipase $A_2$ enzymatic activity (70-80° C.), but unexpectedly it was determined that the preferred reaction temperature is from about 50° C. to about 55° C. Other suitable temperatures may be determined with routine experimentation by one of ordinary skill in the art depending on the specific reaction mixture employed in the phosphoglyceride hydrolysis reaction.

The time for the reaction may be chosen by the user of the method as is convenient, so long as the hydrolysis of phosphatidylcholine has progressed to an extent desired. It should be noted that the previous methods of PC hydrolysis by phospholipase $A_2$ proceeded to complete conversion of PC to LPC in several days. In the presently disclosed methods, the hydrolysis of PC can be completed in several hours. This reduction in reaction time is entirely unexpected in view of the significantly lesser surface area of the ungranulated solid matrix PC used in the reaction to produce LPC as compared to the surface area of granulated PC materials used in previous methods. It is preferred that the reaction proceed for 24 hours or less, more preferably for less than 12 hours, still more preferably for less than 6 hours, and most preferably for less than 4 hours.

The amount of phosphatidylcholine to be used in the method of the invention is quantified as a weight percentage of the total solids in the reaction mixture. Weight percentage is calculated by dividing the weight of a single reaction component divided by the sum of the weights of all solid components in the reaction mixture. Previous methods of hydrolyzing phosphatidylcholine to produce LPC, which favored reaction mixtures comprising less than about 40% phosphatidylcholine by weight due to the likelihood that reaction mixtures with greater percentages of PC were likely to separate into a non-lamellar two-phase system which does not permit efficient hydrolysis of the phosphatidylcholine. In contrast the present methods, which provide hydrolysis of ungranulated, solid matrix PC to produce LPC, can accommodate weight percentages of PC that are greater than or equal to 40% of the total solids in the reaction mixture.

Preferably the reaction mixture is formed in a reactor device that mixes, stirs, and/or heats the reaction mixture. The mixing and stirring of the reaction mixture is believed to bring the phospholipase $A_2$ (and other reaction components) into contact with the solid matrix of phosphatidylcholine, thereby increasing the efficiency of the hydrolysis reaction and reducing the time required for complete hydrolysis. One example of a suitable reactor device is the Model M5 (½ HP motor) mixer of Littleford Day Inc. (Florence, Ky.). This mixture has a 5 liter capacity. Other similar reactors having larger capacity can be used to scale up the reaction.

The reactors also can provide heating and drying functions. The reaction mixture can be heated to optimal reaction temperatures, which typically depend on the temperature optimum of the enzyme. Heating also can be employed to dry the reaction products after completion of the hydrolysis reaction. Reactors can be equipped with other functions to aid drying, such as vacuum. The reactor can be used to modify the mole ratios of MG and FA to LPC and can be used to change the molecular structure between lamellar and inverse hexagonal organization(s) or combinations thereof. Using the reactor, the inverse hexagonal structure of LXS™ can be formulated with protein, carbohydrate, starch and flavors to produce a powdered formulation of LXS™. The reactor may also be used to form a drug/LYM-X-SORB™ inclusion complex.

An agent may be added to the mixture at any weight percentage which enhances the hydrolysis of phosphatidylcholine over the amount of hydrolysis of phosphatidylcholine alone by phospholipase $A_2$. Most preferably, the agent is monoglyceride. When present in the reaction mixture, virtually any amount of monoglyceride will enhance the hydrolysis of phosphatidylcholine by phospholipase $A_2$. Preferably the molar ratio of phosphatidylcholine:monoglyceride is 1:0.1-1:10. To reach high yields of lysophosphatidylcholine it is preferred to have a molar ratio of phosphatidylcholine: monoglyceride of about 1:1-1:5. Most preferably, the molar ratio of phosphatidylcholine:monoglyceride is about 1:3.

The desired end products of the reaction of phosphatidylcholine and agent with phospholipase $A_2$ are lysophosphatidylcholine alone, a combination of lysophosphatidylcholine with fatty acid or agent, or lysophosphatidylcholine in combination with fatty acid and agent. In particular, when the agent is monoglyceride, a preferred end product is a lipid matrix comprising lysophosphatidylcholine, monoglyceride and fatty acid. The utility of this lipid matrix has been disclosed, for example, in U.S. Pat. Nos. 4,874,795 5,314,921 and 5,972,911.

Where the end product is a lipid matrix composition of lysophosphatidylcholine, monoglyceride and fatty acid, it is preferred that the constituents of the lipid matrix be present in the molar ratio of lysophosphatidylcholine:the sum of monoglyceride and fatty acid of about 1:3 to 1:12. Most preferably, the molar ratio of lysophosphatidylcholine:the sum of monoglyceride and fatty acid is about 1:5-1:6. It is also preferred that the individual components of the lipid matrix are present in particular molar ratios in relation to one another. Thus, it is preferred that the molar ratios of lysophosphatidylcholine:monoglyceride:fatty acid are 1:4:2-1:2:4. Most preferably, the molar ratios of lysophosphatidylcholine:monoglyceride:fatty acid are either 1:4:2, 1:3:3 or 1:3:2.

Additional monoglycerides and fatty acids may be added to the lysophosphatidylcholine/monoglyceride/fatty acid mixture and melted or mixed to yield compositions of matter as defined in U.S. Pat. No. 4,874,795. Thus, monoglyceride and/or fatty acid may be added to the lipid matrix if it is desired to alter the molar ratios of monoglyceride and/or fatty acid to yield a desired product.

The lipid matrix produced by the method of the invention is useful for, inter alia, delivery of drugs. When so desired, a pharmaceutical composition may be added to the reaction mixture, for inclusion in the lipid matrix, at any time which does not adversely affect the integrity of the pharmaceutical composition. Preferably the desired pharmaceutical composition is added subsequent to the formation of the lipid matrix and/or during the transition between the lamellar and inverse hexagonal organization(s).

Preferably the methods disclosed herein include a step of recovering from the reaction mixture the lysophosphatidylcholine formed in the reaction mixture. As used herein, "recovering" means recovering the lysophosphatidylcholine from one or more of the components of the reaction mixture. The actual form of the lysophosphatidylcholine can vary, i.e., the lysophosphatidylcholine recovered can be recovered complexed with other components of the reaction mixture. For example, recovering lysophosphatidylcholine includes recovering a lipid complex which contains lysophosphatidylcholine, fatty acid and agent. Recovering lysophosphatidylcholine also embraces recovering lipid complexes which contain lysophosphatidylcholine and agent or lysophosphatidylcholine and fatty acid. It is not necessary that the lysophosphatidylcholine or lysophosphatidylcholine-containing lipid complex be purified to be considered recovered. Therefore, the lysophosphatidylcholine or lysophosphatidylcholine-containing lipid complex can contain other constituents present in the reaction mixture, such as $Ca^{2+}$ or phospholipase $A_2$. The lysophosphatidylcholine, however, when "recovered" is sufficiently isolated from other materials so as to be useful as an isolate of lysophosphatidylcholine or of a lysophosphatidylcholine-containing lipid complex. The lysophosphatidylcholine or lysophosphatidylcholine-containing lipid complex which is recovered can, however, be purified if so desired.

The step of recovering can include one or more process steps whereby lysophosphatidylcholine is separated from one or more of the constituents of the reaction mixture. Thus, lysophosphatidylcholine may be separated from fatty acid, agent (e.g. monoglyceride) or fatty acid and agent. Separation includes separation of the desired lysophosphatidylcholine or lysophosphatidylcholine-containing lipid complex from the reaction mixture as well as separation of an unwanted reaction component from the reaction mixture. For example, the reaction mixture can be extracted with acetone to preferentially separate lysophosphatidylcholine from other reaction mixture components, as described herein. In other embodiments, where a lipid matrix comprising lysophosphatidylcholine, monoglyceride and fatty acid is the desired end product, other reaction components such as phospholipase $A_2$, water, organic solvents and excesses of monoglyceride or fatty acid can be separated from the lipid matrix. Alternatively, water can be separated from other reaction mixture components by heating or drying the reaction mixture as is described herein. Other methods of separating selected products of the enzymatic hydrolysis of phosphatidylcholine are provided herein, and still others will be known to one of ordinary skill in the art.

Many methods known to those of ordinary skill in the art will be applicable to separation of lysophosphatidylcholine from other reaction components based on differential solubilities, molecular weights, molecular sizes or other properties. For example, lysophosphatidylcholine may be separated from other components by preparative chromatography. Preferably, lysophosphatidylcholine can be separated by extraction of the reaction mixture with acetone. This method relies on the insolubility of phospholipids in acetone; lysophosphatidylcholine precipitates as a solid which is easily recovered from other reaction constituents. Other separation methods will be known to those of ordinary skill in the art.

Compositions containing lysophosphatidylcholine, alone or in combination with monoglyceride and/or fatty acids, are useful as emulsifiers, antioxidants and surfactants in cosmetic and dermatological preparations.

As disclosed above, the methods of the invention also contemplate the removal of water and/or other solvents from the reaction mixture to recover desired end products. Thus, the method of making any of the foregoing products may include the removal of water or solvents as part of, or separate from, the separation processes outline above.

Any method known in the art for the removal of water, aqueous solvents, or mixtures of aqueous and organic solvents may be used so long as the desired end products of the hydrolysis reaction are not adversely affected. It is preferred that methods which are scalable to industrial production of lysophosphatidylcholine or lipid matrix compositions be employed. For example, solvents may be removed from desired end products by heating, vacuum, lyophilization, or spray drying processes. Such methods may be employed for such a time and to such an extent so as to remove all or part of the water or solvent mixtures as desired by the user. Preferably, reaction products are heated to remove water, thereby yielding a paste of lysophosphatidylcholine or lipid matrix.

Figure 9A:
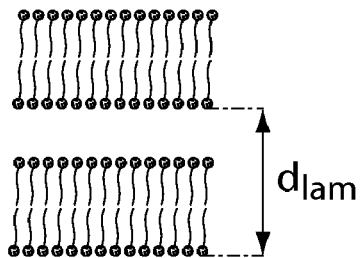
FIG. 9A shows a schematic representation of a lipid matrix in lamellar phase.
Figure 9B:
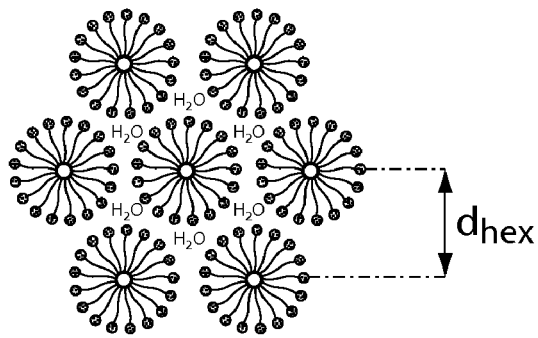
FIG. 9B shows a schematic representation of a lipid matrix in hexagonal phase.

In another aspect of the invention, a lipid matrix having certain physical properties is provided. Upon addition of water to a neat lipid matrix of lysophosphatidylcholine, monoglyceride and fatty acid with heating, the physical properties of the matrix change to include increased viscosity and altered X-ray diffraction patterns. At a molar ratio of 8 moles water per mole of lipid matrix, all of the lipid matrix becomes converted to the new form. As described in the Examples, the data are consistent with conversion of a lamellar bilayer structure to a hexagonal structure with the addition of water and heat. The X-ray data favors an inverse hexagonal structure, with the matrix organized to have its polar hydrophilic region on the interior of matrix molecules. The data is also consistent, however, with a hexagonal structure wherein the matrix is organized to have its polar hydrophilic region on the exterior of matrix molecules (see FIGS. 9 and 10).

Thus the invention includes methods for making hexagonal phase lipid matrices by contacting a neat lipid matrix with water and heat. Preferably the matrix is mixed during or after the addition of water. In preferred methods, one or more pharmaceutical compounds are included in preparation of the hexagonal phase matrix, such as by adding the compounds during the addition of water to the neat lipid matrix. Alternatively, the pharmaceutical compounds can be added after the formation of the hexagonal matrix is complete, optionally after the formation of particles of desired size (e.g., by sonication in the presence of bicarbonate or other suitable ions as known to one of ordinary skill in the art).

One feature of the hexagonal matrix so formed is that it can be used as a carrier or delivery vehicle for pharmaceuticals that are hydrophobic and/or hydrophilic. The hexagonal matrix is believed to be particularly suited for delivery of nucleic acids and vaccine constituents. For example, a delivery vehicle for hydrophobic and hydrophilic pharmaceuticals can be prepared by including a hydrophilic compound during the preparation of the hexagonal lipid matrix particles, whereby the hydrophilic compounds become incorporated into the interior of inverse hexagonal lipid matrix particles, interacting with or binding to the polar hydrophilic region. Hydrophobic compounds can then be added to associate with or bind to the outside of the inverse hexagonal lipid matrix particles (the nonpolar hydrophobic region of the lipid matrix). If non-inverse hexagonal particles are formed, then the order of addition of hydrophobic and hydrophilic compounds may be reversed.

Another use of the compositions described herein is as nutritional supplements. As will be known to one of ordinary skill in the art, lipid matrices have been used for nutritional supplements, particularly to supplement the diet of subjects having particular disorders that require additional nutrition, such as wasting diseases, cancer and cystic fibrosis. One recent study has shown that a lipid matrix can be used effectively in the treatment of cystic fibrosis patients (Lepage et al., *J. Pediatr.* 141:178-185, 2002, incorporated by reference). Thus, the present invention includes the use of the compositions described herein for the treatment of disease by improving the nutritional status of patients, using methods as are known to one of ordinary skill in the art, such as the Lepage reference.

In particular, methods for treating cystic fibrosis are provided. The methods include administering to a subject in need of such treatment an effective amount of the compositions described herein. The treatments favorable affect a physiological parameter of the subject related to the cystic fibrosis. Preferred physiological parameters include height-for-age Z score, weight-for-age Z score, forced expiratory volume, energy intake from diet, essential fatty acid status, fat soluble vitamin status and retinol binding protein status. Thus the invention also provides nutritional supplements that include an effective amount of any of the foregoing compositions. The nutritional supplements can be formulated according to standard methodology in the pharmaceutical and nutritional arts, for example as described in Example 3 below.

EXAMPLES

Example 1

Preparation of Lysophosphatidylcholine and Lipid Matrix Compositions

Hydrolysis of Solid Phosphatidylcholine

Briefly, using a more economical, solid matrix, ungranulated form of soy PC (Nattermann 8729, Nattermann Aventis Pharma Deutschland GmbH, Cologne, Germany) and an efficient mixing apparatus (Littleford/Day reactor, Model M5, ½ HP motor, 5 L capacity, Littleford Day Inc., Florence, Ky.), the hydrolysis of PC to lysophosphatidylcholine (LPC) using phospholipase $A_2$ and monoglyceride (MG) was complete (>99%) within 5-6 hours. In the following experiments 400 g of Nattermann 8729 were hydrolyzed in a 5 L Littleford/Day reactor. The load phospholipid, monoglyceride, phospholipase $A_2$ enzyme, buffer and water represented approximately 40% of the 5 liter capacity of the reactor.

In the hydrolysis of phosphatidylcholine (PC) using the enzyme phospholipase $A_2$ ($PLA_2$) (Lecitase, Novo Nordisk, Denmark), approximately 300,000 Lecitase Units (one unit produces 1 μmole of fatty acid per minute) were used to hydrolyze 400 g of Nattermann 8729 in the presence of monoglycerides (MG) (Dimodan™ LSK and Dimodan™ OK, Danisco Cultor, New Century, Kans.). The initial mole ratio of the sum of PC+LPC:MG was 1:3. Time for complete hydrolysis was 4 to 5 hours (batch 5.06; see Table 1). As shown in FIG. 1, PC hydrolysis was present at 4 hours and absent at 5 hours. Also note that the moles of fatty acids (FA) were always higher than the corresponding moles of lysophosphatidylcholine (LPC) when in fact they should be equivalent as one mole of PC is hydrolyzed to 1 mole of LPC and 1 mole of FA (1 PC→1 LPC+1 FA). Reaction products were determined by HPLC analysis.

Figure 2:
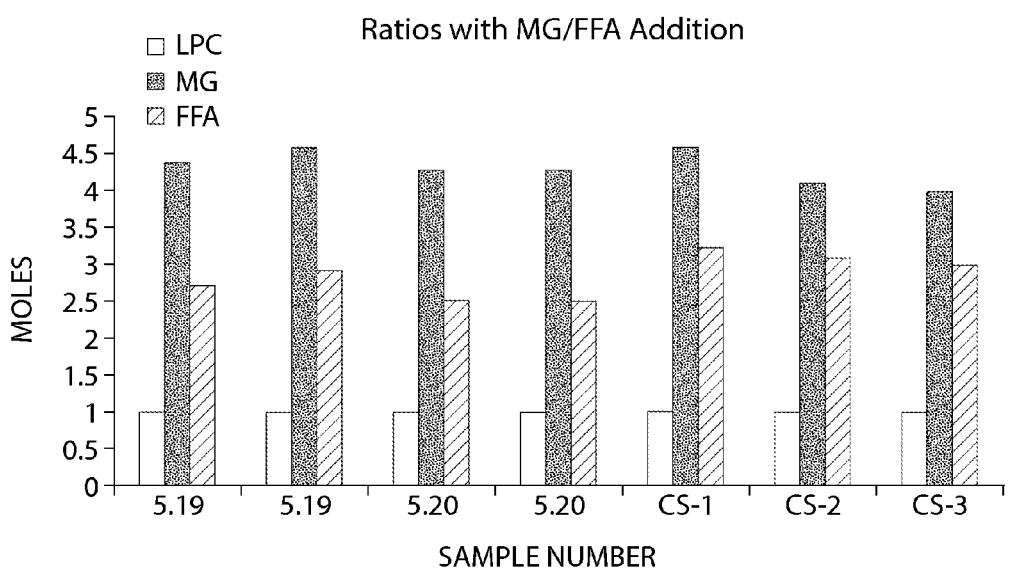
FIG. 2 depicts the composition over time of the phosphatidylcholine hydrolysis reaction mixture with monoolein added at a 1:3 molar ratio.

Based upon the addition of reactants, the final lipid matrix preparation should have a theoretical mole ratio of 1:4:2 (LPC:MG:FA); whereas, in fact both the MG and FA were greater in the tested preparations. As shown in FIG. 2, the mole ratio of MG exceeded 4 and FA also exceeded its theoretical value of 2. In calculating these results the concentration of LPC was the base of 1. Batches 5.19 and 5.20 (both analyzed in duplicate), and batches CS-1, CS-2 and CS-3 contained the same level of enzyme and reactants as noted above.

To explain the increased mole ratios of both MG and FA, a loss of LPC was hypothesized to occur during the hydrolysis of PC to yield glycerylphosphorylcholine (GPC). This could occur by inappropriate hydrolysis of 2 fatty acids from PC, or by hydrolysis of a fatty acid from LPC, as follows: 1 PC→GPC+2 FA or 1 LPC→1 GPC+1 FA.

Effect of Fatty Acid Addition to Reaction Mixture

In the hydrolysis of PC using $PLA_2$, the maximum rate of hydrolysis is delayed and this delayed time (tau) can be reduced by adding both LPC and FA (Bent and Bell, *Biochimica et Biophysica Acta* 1254:349-360; 1995).

In Nattermann 8729, there is about 4.5% LPC but no FA. Therefore, the effect of adding fatty acids to the initial reaction mixture was tested.

GPC production was evaluated in four batches without any added FA (5.21A, 5.21B, 5.23, 5.24). Batch 5.21A was a control in which unaltered hydrolysis was performed as described above. This batch was vacuum dried to 1.34% water. Batch 5.21B was like 5.21.A, except that calcium was added (0.5 moles) and the amount of water was increased to 1.95% (±2 moles). Batch 5.23 was like 5.21.A, except that 40 ml concentrated HCl was added after PC hydrolysis; this batch was vacuum dried to 0.67% water. Batch 5.24 was like 5.21.A, except that 40 ml concentrated HCl was added after PC hydrolysis; this batch was vacuum dried to about 1.70% water (±2 moles).

The amounts of GPC in the four batches was analyzed by phosphorous NMR. Samples 5.21A and 5.21B contained 16.67 and 19.80 mole % of GPC and samples 5.23 and 5.24 contained 8.96 and 9.93 mole % of GPC. Therefore, the addition of acid (HCl) decreased the amount of GPC in the batches by about 50%.

In contrast, the addition of 15 mole % of fatty acid (0.09 moles) to the initial reaction mixture prior to hydrolysis (batch 5.25) showed zero yield of GPC. Surprisingly, the complete hydrolysis of PC as analyzed by HPLC (using 300, 000 units of enzyme) occurred within 2 hours without production of GPC (as analyzed by phosphorus NMR). Thus, the addition of fatty acid both reduced the production of GPC as well as decreased the time for complete hydrolysis of PC, which it believed to correspond to the reduction of tau.

In these initial studies, approximately 300,000 units of $PLA_2$ were used and there is a need to reduce the cost of the PC hydrolysis and lipid matrix preparation. Therefore, decreased enzyme levels were evaluated in hydrolysis reactions as described above.

In batch 5.27, 150,000 units of $PLA_2$ enzyme (without adding FA to the reaction mixture) showed complete hydrolysis of PC within 5.5 hours. Using only 72,000 units of $PLA_2$ (batch 5.30, without FA) PC hydrolysis was complete within 6-7 hours.

The addition of fatty acid reduced the time for complete hydrolysis of PC. Using 150,000 units of $PLA_2$ with added FA, the hydrolysis of PC required approximately 2.75-3 hours (batches 5.28 and 5.29) in contrast to 5.5 hours, noted above for batch 5.27. Using 120,000 units of enzyme with added FA, hydrolysis was complete within 3-4 hours (batches 5.33 and 5.32).

Therefore, the units of $PLA_2$ can be significantly reduced without drastic effects on the reaction time. The effect on reaction time is reduced by the addition of fatty acids.

Effect of Mixing on Reaction

A newer Littleford/Day 5 liter reactor (Model M5, 1 HP motor) that has a more powerful motor was tested under the same reaction conditions described above. After the first batch using a 40% load it was apparent that the maximum reaction capacity of 70% load would be possible.

Using the new 5 liter reactor with a 40% load, approximately 120,000 units of $PLA_2$ enzyme and added FA, the hydrolysis of PC was complete within 2.25 hours (batch 5.34) which contrasts with 3-4 hours noted above for the old reactor.

Using the same reactor with a 70% load and proportionately the same 120,000 units of $PLA_2$ and added FA, the hydrolysis of PC was complete within the same time, 2.25 hours (batches 5.35 and 5.37).

In summary, the addition of fatty acids (FA) to the initial reaction mixture increased the yield of lysophosphatidylcholine (LPC) and reduced the time required for complete hydrolysis of phosphatidylcholine (PC). The increased efficiency of the $PLA_2$ enzyme with added FA also permits the use of decreased enzyme concentrations for the hydrolysis of PC. Efficiency of mixing as gauged by the use of a more powerful mixer also contributed to reduced reaction time, regardless of the load status (up to maximum fill capacity; i.e., 70% for Model M5) of the mixer.

TABLE 1

| BATCH # | ADDED FA | ENZYME UNITS | TIME-HR 100% HYDROL. | GPC MOLE % |
|---|---|---|---|---|
| ½ HP REACTOR | | | | |
| 5.06 | NONE | 300,000 | 4 TO 5 | ND |
| 5.27 | NONE | 150,000 | ca. 5.5 | ND |
| 5.30 | NONE | 72,000 | 6 TO 7 | ND |
| 5.21A | NONE | 300,000 | 4 TO 5 | 16.67 |
| 5.21B | | | | 19.80 |
| 5.23 | NONE | 300,000 | 4 TO 5 | 8.96 |
| 5.24 | NONE | 300,000 | 4 TO 5 | 9.93 |
| 5.25 | YES | 300,000 | 2 | 0.00 |
| 5.28 | YES | 150,000 | 2.75 TO 3 | ND |
| 5.29 | YES | 150,000 | 2.75 TO 3 | ND |

TABLE 1-continued

| BATCH # | ADDED FA | ENZYME UNITS | TIME-HR 100% HYDROL. | GPC MOLE % |
|---|---|---|---|---|
| 5.32 | YES | 120,000 | 3 TO 4 | ND |
| 5.33 | YES | 120,000 | 3 TO 4 | ND |
| 1 HP REACTOR | | | | |
| 5.34 | YES | 120,000 | ca. 2.25 | ND |
| 5.35 | YES | 120,000 | ca. 2.25 | ND |
| 5.37 | YES | 120,000 | ca. 2.25 | ND |

ND = Not determined

Example 2

Analysis of Physical Properties of Lipid Matrix Preparations

Birefringent and Rheological Characteristics

Figure 3:
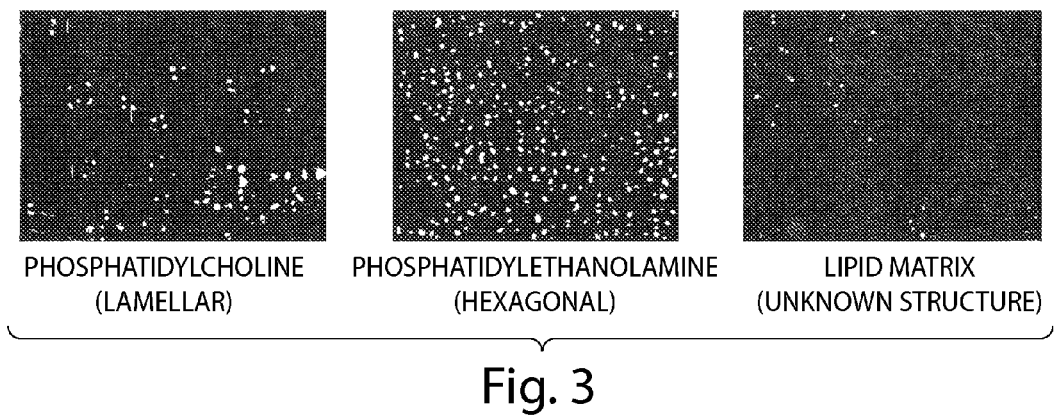
FIG. 3 shows the birefringence characteristics of phosphatidylcholine, phosphatidylethanolamine and basic neat lipid matrix.

Example 1 shows a modification of the method to hydrolyze phosphatidylcholine (PC) and to produce an organized lipid matrix of PC, monoglyceride (MG) and fatty acids (FA). Using the same Littleford/Day reactors [Model M5, ½ HP and 1 HP motors], the 30% water content of the reaction was removed with vacuum and heat within 16-18 hours. The resulting basic neat lipid matrix, when viewed in a polarizing light microscope, exhibited a unique birefringence of unknown structure that was different from the lamellar and hexagonal phases of phosphatidylcholine and phosphatidylethanolamine, respectively (FIG. 3), but may be similar to the birefringent liquid crystalline phases in human intestinal contents during fat digestion (Holt, Fairchild and Weiss, *Lipids* 21:444-446, 1986).

Figure 4:
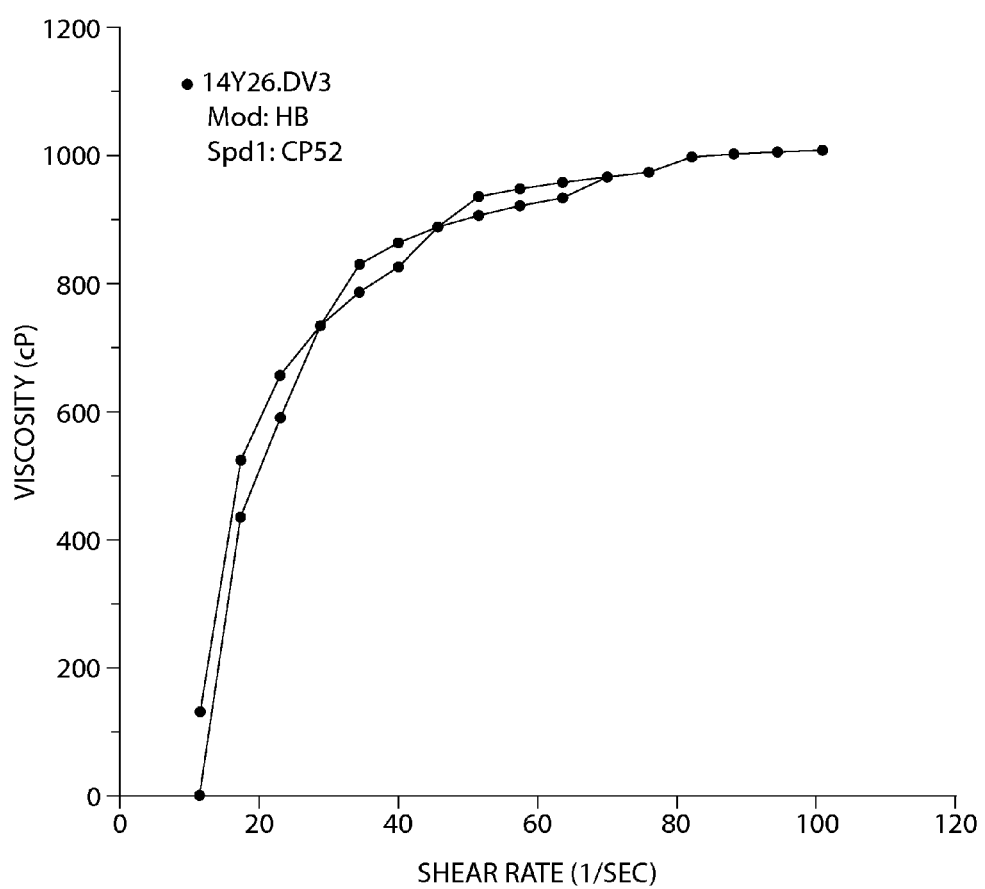
FIG. 4 depicts non-Newtonian flow behavior characteristics of a basic neat lipid matrix containing <1% moisture.
Figure 5:
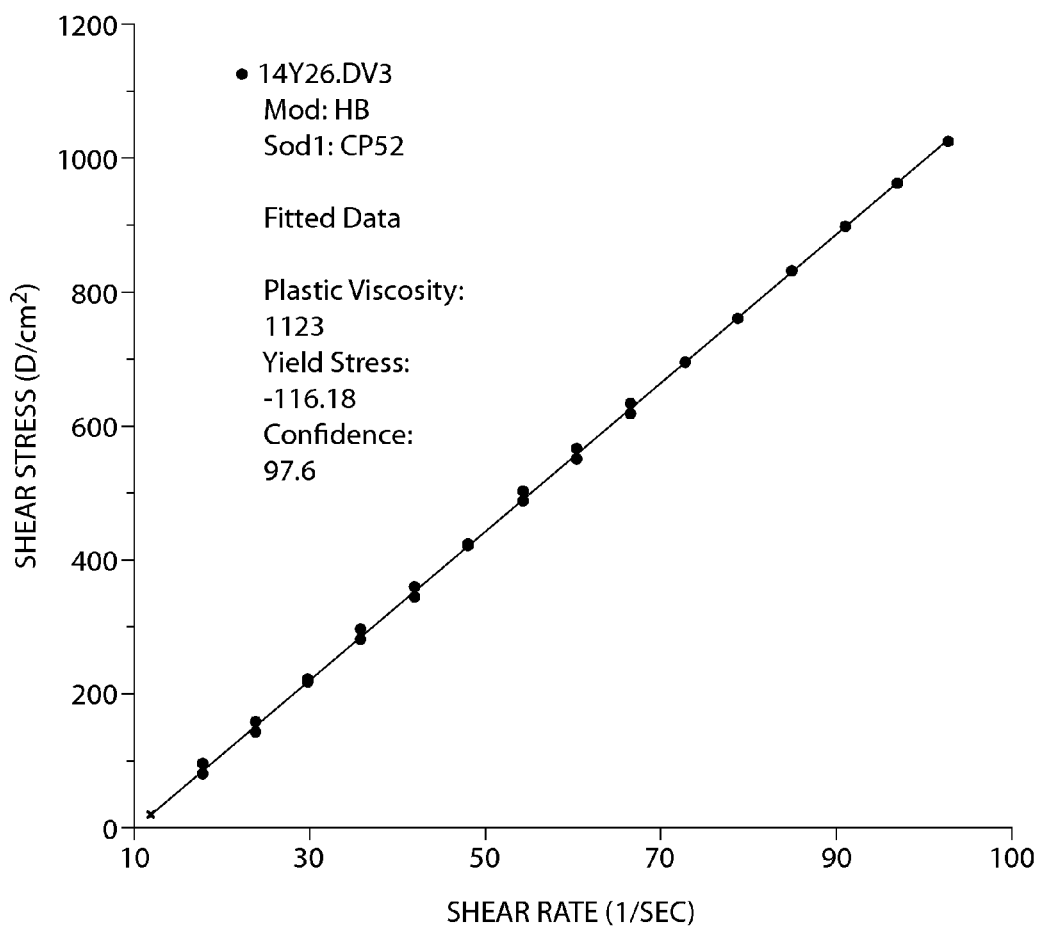
FIG. 5 depicts non-Newtonian flow behavior characteristics of a basic neat lipid matrix containing <1% moisture from measurements taken at 50° C.

Viscosity is the measure of the internal friction of a fluid. As shown in FIGS. 4 and 5, the basic neat lipid matrix containing <1% moisture shows non-Newtonian flow behavior characteristics. A dilatant fluid shows "shear-thickening" flow behavior; i.e., increasing viscosity with an increase in shear rate.

Differential Scanning Calorimetry (DSC)

Figure 6:
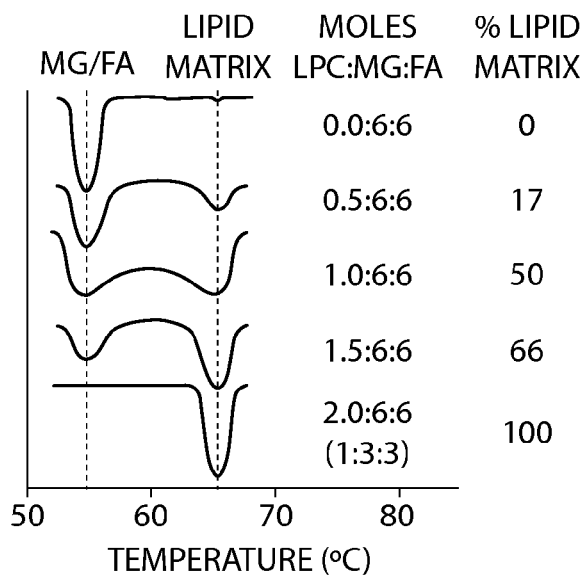
FIG. 6 shows differential scanning calorimetry of varying mole ratios of lipid matrix.

Based upon differential scanning calorimetry (DSC) analysis of a palmitoyl lipid matrix in the presence of excess MG and FA, one mole of LPC will interact with a maximum of 5-6 moles of MG/FA (FIG. 6); i.e., one mole of LPC will form a complex with 3 moles of MG and 3 moles of FA.

Figure 7:
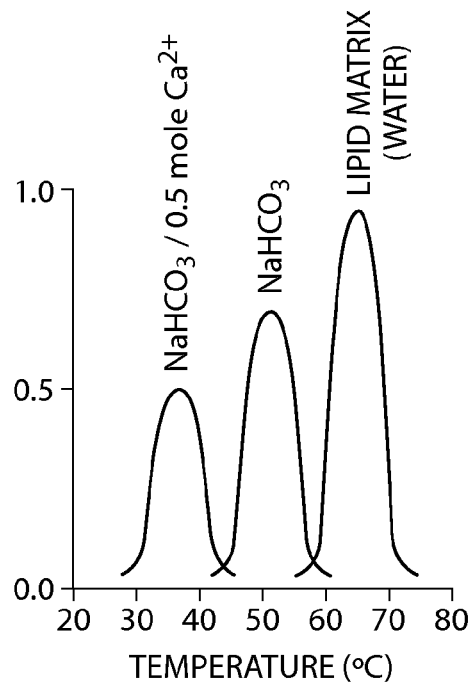
FIG. 7 depicts differential scanning calorimetry analysis of lipid matrix in aqueous media.

Sonication of the protonated lipid matrix yields particles having a size ~150 nm; whereas, sonication of the ionized lipid matrix yields ~70 nm particles (see U.S. Pat. No. 5,891, 466 to Yesair). The DSC analysis of a palmitoyl (16:0) matrix [16:0 LPC (1 mole); 16:0 MG (3 moles); 16:0 FA (3 moles)] that was sonicated in water showed a melting point at 64.6° C., the ionized lipid matrix in 15 mM sodium bicarbonate melted at 52° C. and the ionized lipid matrix containing 0.5 moles of calcium ions per mole of the monomeric lipid matrix had a broad melting peak at about 35-40° C. (FIG. 7). Greater amounts of calcium ions had no further effects.

Viscosity with Variable Water Content

As shown previously, the proposed organization of the lipid matrix has both a polar region and a non-polar hydrophobic region. The former contains phosphorylcholine of LPC, carboxylic acid of FA and glycerol of MG. The space between the polar region of apposed lipid matrix (1 LPC:3 MG:3 FA or variation thereof) monolayers is the region that binds both water, perhaps as water clusters (Gregory et al., *Science* 275:814-817, 1997), and metal ions which can affect an intramolecular stabilization of the lipid matrix.

Viscosity of LYM-X-SORBT™ (LXS™) compositions were measured with a Brookfield viscometer (Model HB, Spindle CP52, Brookfield Engineering Laboratories, Middleboro, Mass.). The LXS™ had a molar ratio of LPC/MG/FA of (1:4:2) and prepared according to U.S. Pat. No. 5,716,814 (Yesair). Water and LXS™ were added to screw-cap vials, heated at 50° C. for a half hour with shaking. The samples were allowed to cool to room temperature.

Figure 8:
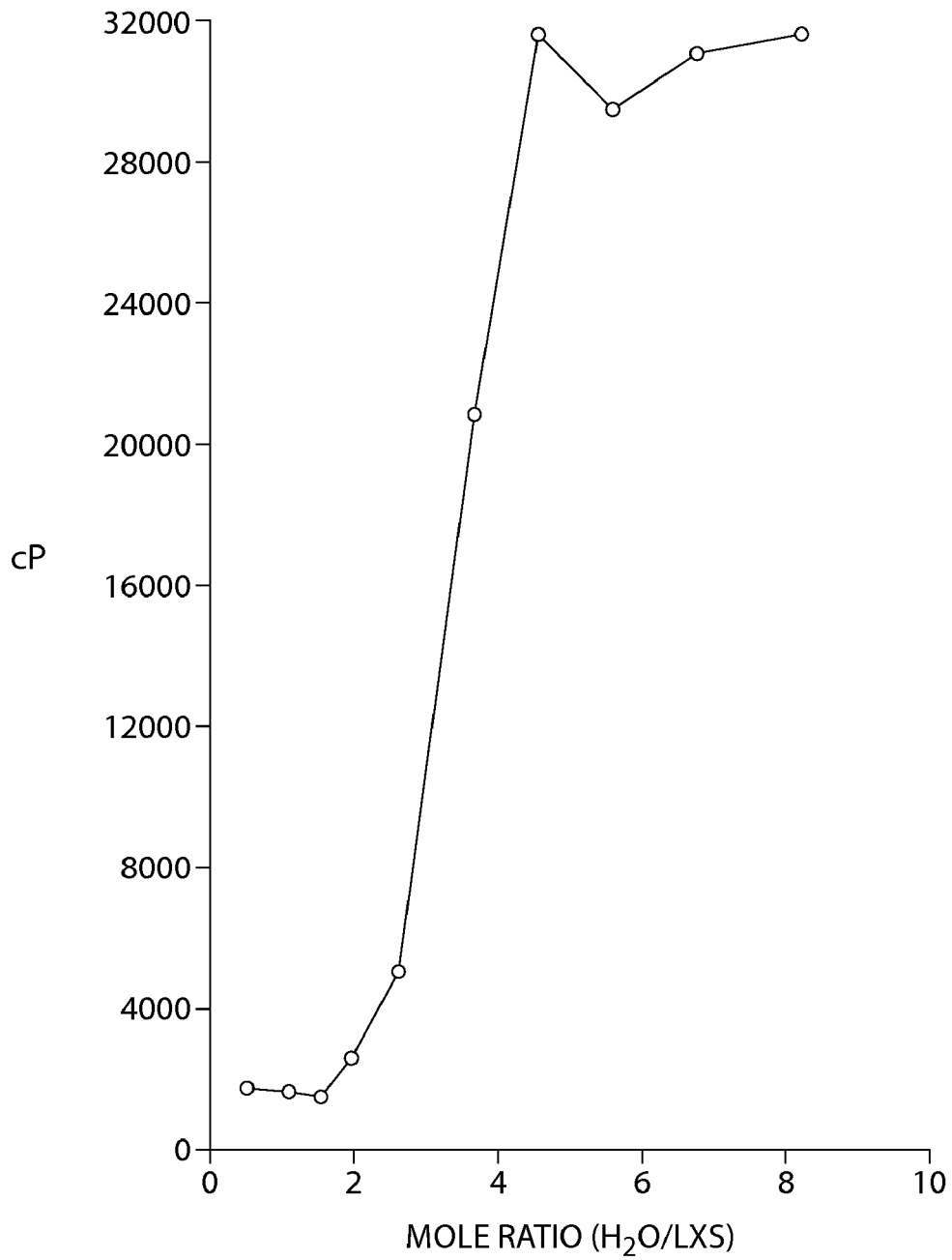
FIG. 8 shows viscosity of LYM-X-SORBT™ with increasing amounts of water.

The viscosity data is listed in Table 2 and plotted against mole ratio of water/LXS in FIG. 8.

TABLE 2

Viscosity of LYM-X-SORB ™ with Variable Water Content

| SAMPLE # | LYM-X-SORB | | WATER ADDED | | MOLE RATIO | VISCOSITY |
| --- | --- | --- | --- | --- | --- | --- |
| | mmol LXS | mmol $H_2O$ | — | mmol $H_2O$ | $H_2O$/LXS | (cP) |
| 6-1 | 4.02 | 2.07 | NONE | 0.00 | 0.51 | 1780 |
| 6-2 | 4.00 | 2.07 | 0.39 | 2.18 | 1.06 | 1633 |
| 6-3 | 4.03 | 2.07 | 0.76 | 4.25 | 1.58 | 1558 |
| 6-4 | 4.03 | 2.07 | 1.02 | 5.78 | 1.95 | 2448 |
| 6-5 | 4.01 | 2.07 | 1.47 | 8.03 | 2.59 | 4971 |
| 6-6 | 4.02 | 2.07 | 2.19 | 12.47 | 3.32 | 20847 |
| 6-7 | 4.02 | 2.07 | 2.77 | 15.90 | 4.47 | 31679 |
| 6-8 | 4.01 | 2.07 | 3.52 | 20.33 | 5.59 | 29379 |
| 6-9 | 4.01 | 2.07 | 4.29 | 24.96 | 6.74 | 30714 |
| 6-10 | 4.01 | 2.07 | 5.25 | 30.80 | 8.20 | 31531 |

It is readily apparent that the addition of water affects changes in the lipid matrix organization as demonstrated by the marked increase in viscosity.

Sample 6-1 is similar to the sample described under the birefringent characteristics section of Example 2. The taste of sample 6-1 was unpleasant with an aftertaste, whereas the taste of sample 6-10 was unremarkable, e.g., bland with no aftertaste. Thus it can be assumed that water can affect some organization within the LXS™ matrix.

X-Ray Diffraction Analyses

In initial x-ray diffraction studies, a neat synthetic lipid matrix containing only the oleoyl (18:1) species of lysophosphatidylcholine (LPC; Avanti Polar Lipids, Alabaster, Ala.), monoglyceride (MG), and fatty acid (FA; Nu-Chek Prep, Inc., Elysian, Minn.) with a molar ration of 1:4:2 was evaluated. Based upon the viscosity changes of the lipid matrix upon the addition of water (see FIG. 8), this lipid matrix containing ~0, 1, 3, or 8 moles of water per mole of matrix monomer was evaluated. In the neat (0.2% water) synthetic lipid matrix (18:1 species), the x-ray diffraction pattern [obtained by Prof. Thomas McIntosh (Duke University)] displayed 6 reflections that index as the first 6 orders of a lamellar (bilayer) spacing of 5.0 nm (50 Å, $d_{lam}$, see FIG. 9A). Also present were several sharp wide-angle reflections at 0.46, 0.43, and 0.40 nm corresponding to the spacing of the hydrocarbon chains. Sharp wide-angle reflections are characteristic of solid (gel) phase bilayers (see FIG. 9A). In addition, there was also present a 3.35 nm (33.5 Å, $d_{hex}$ see FIG. 9C) low-angle reflection and a 0.45 nm wide angle reflection which correspond to fluid hexagonal phase.

The fully hydrated sample (8 moles water/mole lipid matrix) was analyzed by x-ray diffraction as well as by light microscopy with crossed-polarizers. The hydrated sample was highly birefringent with large regions of striations or brush patterns. Because of this intense birefringence this phase can not be cubic phase as might have been predicted by the high viscosity of the hydrated lipid matrix. The striations are typical of hexagonal phases. In over-exposed x-ray patterns the sole wide-angle reflection is a broad band at 0.45 nm, consistent with melted hydrocarbon chains. There are no indications of sharp wide-angle reflections. However, a very weak low-angle reflection was detected with long exposures at 1.94 nm in addition to the extremely strong reflection at 3.35 nm. The spacings of these two low angle reflections have the ratio of the square root of three, expected for the first two orders of a hexagonal phase. Moreover, when using a fine, focused x-ray beam the 3.35 nm reflections are recorded on a hexagonal lattice. Thus, the fully hydrated synthetic lipid matrix is completely hexagonal (See FIG. 9B, 9C for schematic representations).

The samples containing 1 and 3 moles water per mole lipid matrix had similar low-angle and sharp wide-angle reflections as noted for the solid (gel) phase bilayer but much weaker than observed in the neat lipid matrix. Thus, the samples with 1 and 3 moles water per mole of lipid matrix contained both solid (gel) phase bilayer and hexagonal phase. The bilayer phase was more prominent in the sample containing 1 mole water per mole lipid matrix whereas the hexagonal phase was more apparent at 3 moles water per mole lipid matrix.

Based on the analysis described above, the addition of 8 moles of water to the lamellar, bilayer structure of neat lipid matrix with heat affects a complete structural rearrangement to the hexagonal phase. X-ray data was collected at room temperature indicating the hexagonal phase was also stable at the lower temperature.

Thus the hexagonal phase was present in the "neat" (0.2% water) lipid matrix, increasing with additional moisture content (1 and 3 moles of water per mole of lipid matrix) until only the hexagonal phase was apparent at 8 moles per mole lipid matrix. Since varying amounts of a hexagonal phase were present in all tested lipid matrix compositions, including compositions of very low water content, it is possible that the water was not evenly distributed in the lipid matrix but was distributed as 8 moles per mole lipid matrix in the hexagonal phase and 0 moles per mole lipid matrix in the lamellar phase. Alterations in the equilibrium of the water molecules in the lipid matrix between lamellar and hexagonal phases required an elevated temperature and time.

Figure 9C:
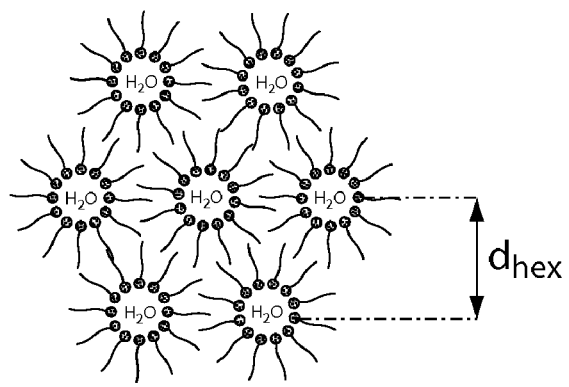
FIG. 9C shows a schematic representation of a lipid matrix in inverse hexagonal phase.
Figure 10:
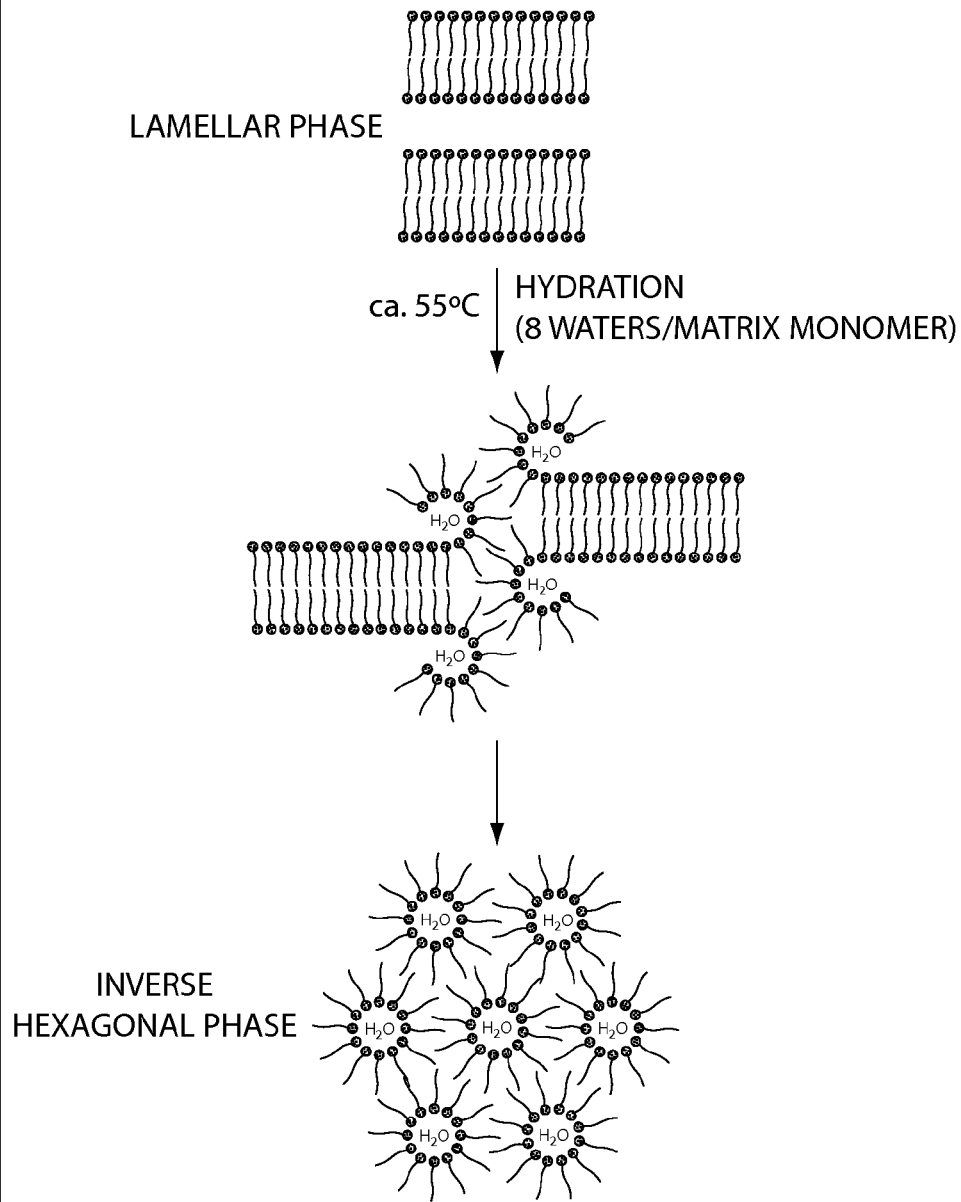
FIG. 10 depicts the structural rearrangement from lamellar phase to hexagonal phase.

The hexagonal phase can potentially organize as a normal hexagonal (FIG. 9B) or as an inverse hexagonal (FIG. 9C). The inverse hexagonal (FIG. 9C) is probably more consistent with the hexagonal lattice spacing ($d_{hex}$) of 33.5 Å observed from the x-ray patterns. Also, the inverse hexagonal phase is consistent with the geometrical arrangement of the lipid constituents having a small head group relative to the hydrocarbon chains. This structural rearrangement from lamellar to hexagonal is shown in FIG. 10. The addition of water with heat to the lamellar lipid matrix may provide the necessary energy to affect this lamellar-hexagonal transition.

The methods used by Rand & Fuller (*Biophys J.*, 66:2127-2138, 1994) to characterize the transition of dioleoylphosphatidylethanolamine (DOPE) from a lamellar phase to a hexagonal phase are employed to provide insight into the organized lamellar and hexagonal structures of the lipid matrix. Understanding this phase transition may be useful in characterizing the taste of the matrix with respect to lipid structure(s) as well as in using the different organized structures for drug delivery.

Structural Integrity of the Lipid Matrix

To correlate the physical properties of the lipid matrix with its composition, the following experiments are performed. First, the structural integrity of protonated and ionized lipid matrix formulations containing varying molar concentrations of water, specifically 0.5, 1.0, 2.0 and 3.0 moles of water per mole of the monomeric lipid matrix (3 moles of water/mole of matrix represents 2.25% water) are determined. Second, the structural integrity of protonated and ionized lipid matrix formulations containing multivalent ions, specifically 0.5; 1.0, and 2.0 moles of ion per mole of the monomeric lipid matrix containing water (possible water content of 0.5, 1.0, 2.0, and/or 3.0 moles of water per mole of monomeric lipid matrix) are determined. The multivalent ions that are tested include calcium, magnesium, iron, and zinc (*Nutr. Rev.*, 42: 220-222, 1984; Koo et al., *Am. J. Clin. Nutr.* 42:671-680, 1985; Koo and Turk, *J. Nutr.* 107:909-919, 1977; *J. Nutr.* 107:896-908, 1977).

The structural integrity of the lipid matrix is evaluated using the following analyses:
  i. Differential scanning calorimetry (DSC)
  ii. X-ray diffraction
  iii. $^{31}$P-NMR
  iv. Polarizing light microscopy and viscosity i. Differential scanning calorimetry (DSC): Based upon preliminary findings, the addition of water to the lipid matrix decreased the melting temperature and the addition of calcium ions further decreased the melting temperature. The effect of water and calcium on the matrix melting point is difficult to rationalize if a single phase were involved; but might be rationalized if water and calcium ion resulted in formation of a different phase (e.g., lamellar-to-hexagonal, lamellar-to-cubic). Thus the characterization of phase transition temperature from ordered to disordered phases of the lipid matrix in the presence of varying water and/or metal ion content provides information for selecting the appropriate compositions and temperature ranges for the x-ray diffraction and P NMR studies.

ii. X-ray diffraction: We have proposed that the organized lipid matrix is lamellar. The electron dense regions of the polar headgroups of the bilayer should be separated by about 30-35 Å, i.e., the length of the non-polar acyl hydrocarbon bilayer. Another possibility based upon the organized structure of LPC (Saunders, *Biochim. Biophys. Acta* 125:70-74, 1966; Hauser, *J. Coll. Interf. Sci.* 55:85-93, 1976) is that the hydrocarbons interdigitate to form a more condensed organization (Hui and Huang, *Biochemistry* 25:1330-1335, 1986).

In either organization the electron dense regions of apposed polar headgroups would be separated by about 20-25 Å. There is also the possibility that both types of structures exist in the more complex organization of a cubic phase. Varying the water and ion content of the lipid matrix will probably modulate the distances between apposed polar regions. The presence of metal ions may also affect a phase change as well.

iii. $^{31}$P-NMR: The resonance characteristics of phosphorus in the LPC headgroup are influenced by the proximity of charged compounds within the bilayer (e.g., chorine, fatty acids) and the proximity of the groups within the apposing bilayer. The molecular distance between the bilayers can be influenced by the presence of water, the protonation of the polar headgroups, and the salt formation of the phosphate group with metal ions.

iv. Polarizing light microscopy and viscosity: Both of these analyses provide data on the structural integrity of the lipid matrix (Robinson and Saunders, *J. Pharm. Pharmacol.* 11:304-313, 1959; Rosevear, *J. Amer. Oil Chem. Soc.* 31:628-639, 1954) and also provide utilitarian measurements for recognizing those structural features having desirable taste profiles. Both of these analyses represent test completion times of less than 30 minutes and thus would be useful in defining the endpoint of the reaction process for producing the optimum lipid matrix.

The foregoing test methods are used to identify those parameters which predict the most stable structural integrity of the lipid matrix and provide insight into the organization (intramolecular stabilization) of such a lipid matrix.

Example 3

LYM-X-SORB™ Uses

Palatable Taste Characteristics

The addition of calcium ions and/or water in defined molar ratios relative to the lipid matrix are factors that contribute to a more palatable lipid matrix formulation for use as a nutritional supplement, e.g. LYM-X-SORB™ (BioMolecular Products, Inc., Byfield, Mass.), for use in cystic fibrosis (CF). It is known that polymorphic changes in PC and MG depend on the thermal history, the rate of cooling, the temperature of equilibrium and other factors (Small, *The Physical Chemistry of Lipids from Alkanes to Phospholipids*, Handbook of Lipid Research 4, Plenum Press, New York, N.Y., 1986, pp. 386-392, 475-517). Thus, the physical chemistry of the product needs to be better defined in order to control the final palatability of the organized lipid matrix. Using the analytical methods described above (x-ray diffraction, differential scanning calorimetry and phosphorus NMR data analysis), the phase behavior and organization (intramolecular stabilization) of the lipid matrix in the presence of water and metal ions is assessed and compared to palatability of the lipid matrix formulations to determine the composition and physical properties of the most palatable lipid matrix formulations.

For example, the taste profiles that were noted in Example 2 for Samples 6-1 and 6-10, can be correlated with the X-ray diffraction analysis (Example 2) for comparable LXS™ containing similar water content. Sample 6-1, low water content and undesirable taste, has a lamellar organization. In contrast, sample 6-10 having 8 moles of water per mole LXS and good taste, is expected to have an inverse hexagonal organization. It is reasonable to conclude that the polar head groups affect the undesirable taste profile and that burying the polar head groups within the hydrophobic regions minimizes the undesirable taste of the head groups.

The lipid matrix (LYM-X-SORB™) can be formulated with protein, starch/carbohydrate, and flavors as wafer bars, candy bars, spray-dried products and ice cream. These non-lipid components, however, can also reduce the undesirable taste of the lipid matrix. The formulation of an intramolecularly stabilized lipid matrix nutritional supplement for analysis of physical properties and taste characteristics is initially a dried product containing 33% by weight of the lipid matrix, 18% protein, and 49% carbohydrate, starch and flavors.

Using the Littleford/Day 5 liter reactor, both a basic LXS™ matrix and an acidic LXS™ matrix were premixed with 8 moles of water per mole of LXS™ at an elevated temperature (50-60° C.). To each, a premix of protein (egg white, 25% by weight), sugar (fructose, 25% by weight), and starch (Capsul®, modified corn starch, National Starch and Chemical, Indianapolis, Ind.; 25% by weight) was added, mixed for 15-30 minutes to yield a powdered LXS™ formulation. The taste of the formulation using an aqueous basic LXS™ was bitter, whereas, the aqueous acidic LXS™ was bland. It is presumed that aqueous basic LXS™ had formed a normal hexagonal structure (FIG. 9B) and that aqueous acidic LXS™ had formed an inverse hexagonal structure (FIG. 9C). The inverse hexagonal structure minimizes the surface area of the polar head groups and therefore, might minimize the undesirable taste of these groups.

The ability to use a reactor vessel, such as the Littleford/Day 5 liter reactor, to prepare a powdered LXS™ formulation including the LXS™ lipid matrix, starch, sugars and protein, reduces the loss associated with transferring the LXS™ lipid matrix from a reaction vessel to a second vessel for mixing with the other components of the LXS™ formulation (protein, sugar, starch, etc.). Accordingly, the cost of preparation of the LXS™ formulation is reduced.

The desirable palatable taste characteristics of the lipid matrix are related to measurable physical and structural parameters of the intramolecularly stabilized matrix using the foregoing analytical test methods.

Standard methodology is used to quantitate the mole ratio of LPC/MG/FA of the lipid matrix, the fatty acid profile of the components and the polyunsaturated fatty acid (PUFA) content (e.g., linoleic/linolenic ration of 5:1 and >50% of fatty acid content), moisture and metal ion concentrations, etc. The samples used for taste testing are analyzed for heavy metal and microbial limits. In addition, polarizing light microscopy and viscometry methodologies are used to provide measurements for recognizing those structural features having desirable taste profiles.

Drug Delivery Formulations

In previous drug/LXS™ formulation studies (see U.S. Pat. Nos. 4,874,795; 5,891,466; and 5,707,873), the LXS™ matrix was prepared using highly purified components (LPC, MG and FA in a 1:3:3 mole ratio) containing minimal moisture content (approximately 0.5% by weight). Based upon X-ray diffraction results (see Example 2, above) the organization of the previous LXS™ matrix is likely lamellar and any drug would be included in the hydrophobic region of LXS™ matrix monomeric structure. Based on the surprising results described herein that the organized molecular structure of the hydrated LXS™ (8 moles of water per LXS monomer) is an inverse hexagonal structure, it can be seen that different structurally diverse drugs can be incorporated within the aqueous phase of the inverse hexagonal structure (see FIG. 9C). In addition, the incorporation of drugs within the hydrophobic region of a normal hexagonal structure (see FIG. 9B) would result in more biologically stable drug/LXS™ formulations within the hostile environments of the gastrointestinal tract. Furthermore, the lamellar, normal hexagonal and inverse hexagonal organization of LXS™ compositions containing drug(s) would also be useful for many routes of administration, e.g., dermal, inhalation, suppository, etc.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

All references, publications and patents disclosed herein are incorporated by reference in their entirety.

We claim:

1. A drug delivery composition comprising a lipid matrix and a pharmaceutically acceptable carrier, wherein at least part of the lipid matrix is in a lamellar phase, wherein the lipid matrix comprises lysophosphoglyceride, monoglyceride and fatty acid, wherein the molar ratio of lysophosphoglyceride:the sum of monoglyceride and fatty acid in the lipid matrix is between 1:3 and 1:12.

2. The drug delivery composition of claim 1 wherein the molar ratio of lysophosphoglyceride:the sum of monoglyceride and fatty acid in the lipid matrix is between 1:5 and 1:6.

3. The drug delivery composition of claim 2 wherein the lipid matrix has a lysophosphoglyceride:monoglyceride:fatty acid molar ratio between 1:4:2 and 1:2:4.

4. The drug delivery composition of claim 3 wherein the lipid matrix has a lysophosphoglyceride:monoglyceride:fatty acid molar ratio selected from the group consisting of 1:4:2, 1:3:3 and 1:3:2.

5. The drug delivery composition of claim 1, wherein the lysophosphoglyceride is lysophosphatidylcholine.

6. The drug delivery composition of claim 1, further comprising one or more water soluble or water insoluble pharmaceutical compounds.

7. A nutritional supplement for the treatment of cystic fibrosis comprising an effective amount of the drug delivery composition of claim 1.

8. A nutritional supplement comprising the drug delivery composition of claim 1.

* * * * *